United States Patent [19]

Van Dijk

[11] Patent Number: 4,866,727
[45] Date of Patent: Sep. 12, 1989

[54] ELECTROMAGNETIC SCREENING ARRANGEMENT FOR A LASER

[75] Inventor: Johannes W. Van Dijk, North Ferriby, Great Britain

[73] Assignee: The European Atomic Energy Community, Luxembourg, Luxembourg

[21] Appl. No.: 120,158

[22] Filed: Nov. 13, 1987

[51] Int. Cl.⁴ .......................................... H01S 3/097
[52] U.S. Cl. .................................... 372/81; 372/86
[58] Field of Search ................. 372/55, 38, 81, 86, 372/109

[56] References Cited

U.S. PATENT DOCUMENTS 4,719,641  1/1988  Muller et al. ....................... 372/109

Primary Examiner—William L. Sikes
Assistant Examiner—B. R. Holloway
Attorney, Agent, or Firm—Bacon & Thomas

[57] ABSTRACT

The discharge chamber (LC) of a laser includes a multiple electromagnetic screen in the form of a plurality of vessels (1 and 3 respectively) located one within the other.

7 Claims, 5 Drawing Sheets

ELECTROMAGNETIC SCREENING ARRANGEMENT FOR A LASER

BACKGROUND OF THE INVENTION

The present invention relates to a laser. In some laser applications at least, it would be desirable to control operation of the laser by computer. This, however, can give rise in the case of a pumped laser to the need to protect the computer and any associated circuitry against interference from electromagnetic radiation generated on pumping of the laser; and meeting this need can give rise to considerable practical difficulties to the extent of making it unfeasible to employ the computer.

SUMMARY OF THE INVENTION

It is an object of the present invention to provide a pumped laser comprising a relatively simple but efficacious screening means to prevent undue emission of electromagnetic radiation by the laser; whereby a computer can readily be employed in the immediate vicinity of the laser to control operation of the latter.

There is provided by the present invention a pumped laser characterized in that the discharge chamber comprises a multiple electromagnetic screen in the form of a plurality of vessels located one within the other.

The vessels may be located coaxially in relation to one another, and be sealed together by annular seals disposed at the axial ends of the vessels. The outermost vessel may be directly earthed; and in one embodiment of the invention, two of the vessels are employed.

The laser, in addition to the main electrodes, may employ an array of pre-ionising electrodes; and a discharge between the latter and between the main electrodes may be effected by a discharge circuit controlled by a trigger circuit.

The laser may comprise, for generating the discharge between the main electrodes and also between the pre-ionising electrodes, if used, a pulse generating circuit operating by release of stored electrical energy on closure of a circuit make/break device, and a trigger circuit inductively controlling the pulse generating circuit by controlling operation of said make/break device, the trigger circuit providing the earth return of the circuit discharge and comprising a switch arranged to isolate the trigger circuit from supply on pulsing of the laser, or a current-limiting resistance to prevent the imposition of any undue voltage on the ground return of the trigger circuit arising as a consequence of operation of the pulse generating circuit.

The present invention will now be described, by way of example only, with reference to the accompanying drawings.

DESCRIPTION OF THE PREFERRED EMBODIMENT

The illustrated laser, generally indicated at Ls (FIG. 1), comprises a discharge chamber, generally indicated at DsC. The discharge chamber comprises two vessels in the form of stainless steel tubes 1, 3 located co-axially one within the other with the outer one being directly earthed (see FIG. 6).

Each of the two tubes is provided with three pairs of diametrically opposed, axially directed, access slots for high voltage leads and e.g. to admit cooled gas, if cooling is used, and also to act as inspection or diagnostic ports; the slots of the inner tube 1 being aligned with those of the outer tube 3, and the slots being closable by bolt on covers such as shown at SlC.

The inner and outer stainless steel tubes form a first and second electromagnetic screen for the discharges; the inner tube only takes the gas pressure. Short circuiting the two coaxial vessels did not meet the requirement of providing adequate screening.

Figure 1:
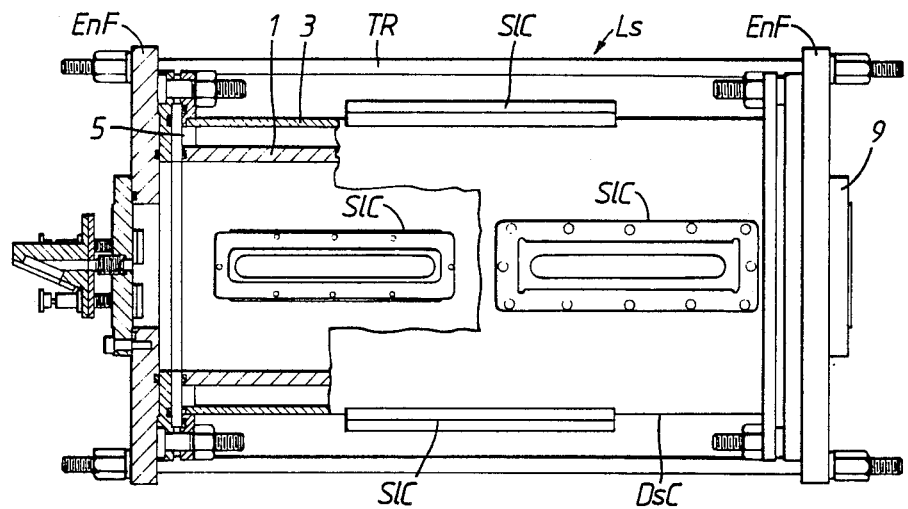
FIG. 1 is a side elevation of a high pressure, pulsed, laser in accordance with the invention, with parts broken away or sectioned to reveal other-wise hidden detail.
Figure 3:
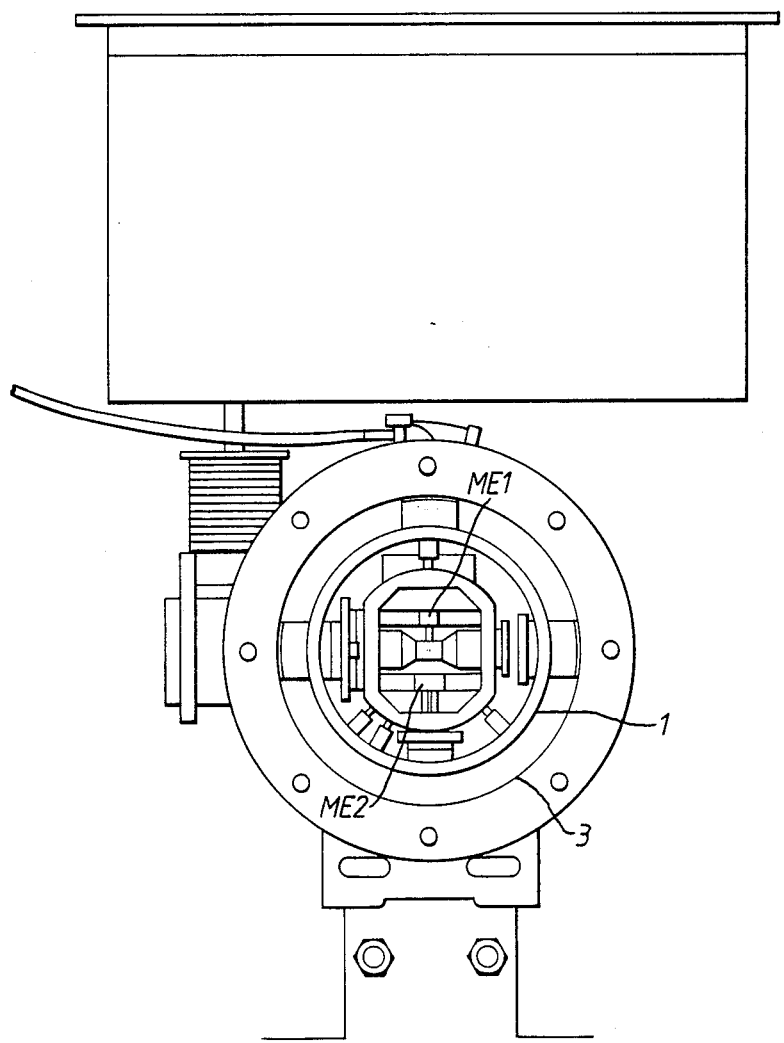
FIG. 3 is a sectional front elevation of the discharge chamber of the laser showing the high voltage feeds thereto.

Two ring sets one of which is seen in FIG. 1 and is generally indicated at 5, seal the space between the stainless steel tubes. This space can accommodate cooling liquid to remove excess heat from the gas reservoir, and the ring sets hold the inner vessel in position. The discharge chamber is faced at either axial and with end flanges EnF held together by tensile rods TR, to withstand the axial pressure, and in the centre the end flanges carry circular ports which are used to mount Brewster windows or resonator mirrors such as indicated at 7. The complete discharge section is seen in FIG. 3 in front elevation. The main lasing volume between the main electrodes ME1, ME2 is preconditioned by four arrays of pre-ionising, sliding spark pins electrodes assembled as a unit, PIU (see especially FIG. 4) to create a weak conducting medium for the main discharge; there being a pair of arrays flanking each of the top and bottom main electrodes. The bottom and top electrodes, which are obscured in FIG. 3 by the P.I.-unit, are placed in their appropriate slot sections and have the facility to be positioned in XYZ directions and to be rotated about an axis parallel to the optical axis. It is possible to adjust the inter-electrode gap pin practise between 4 and 11 mm) with the electrodes n position, by using the reference faces on the electrodes and a custom made jig but without altering in any way the support structure.

Figure 4:
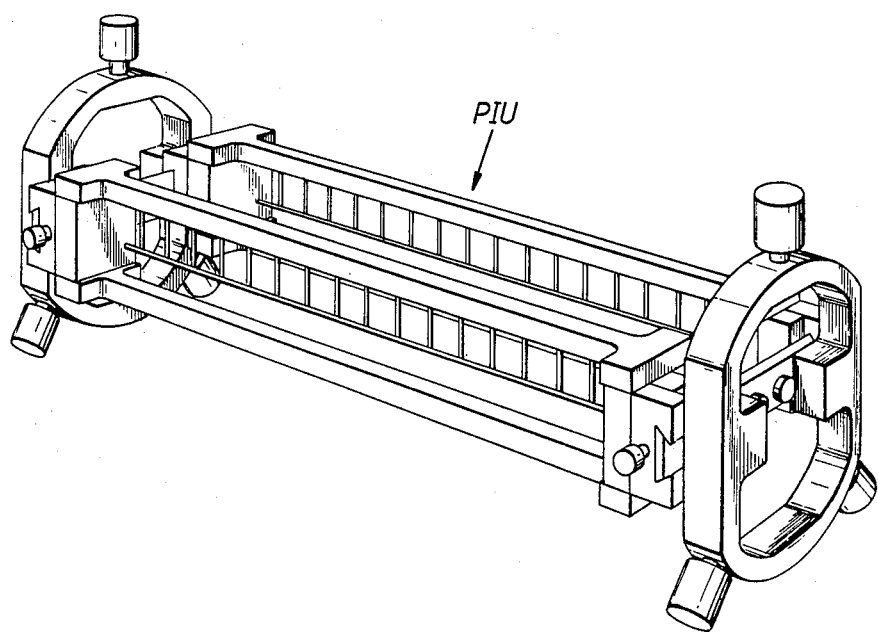
FIG. 4 is a perspective view of a pre-ionising electrode unit employed in the laser of the embodiment.

The PI - unit is shown in FIG. 4. For simplicity the unit seen in FIG. 4 shows two of the arrays of pairs of pre-ioning pins PIP mounted on supporting frameworks FW dovetailed into end blocks EB carried by insulating end frames IF mounted, in use, in the inner tube of the discharge chamber. The assembly, for convenience, could be mounted directly on the main electrodes in a self-synchronizing mode. A design feature here was the ability to alter the P.I. - electrode distance and optimize the preconditioning of the main electrodes with U.V.

photons and to avoid flashover (arcing) between the P.I. unit and main electrodes.

Figure 2:
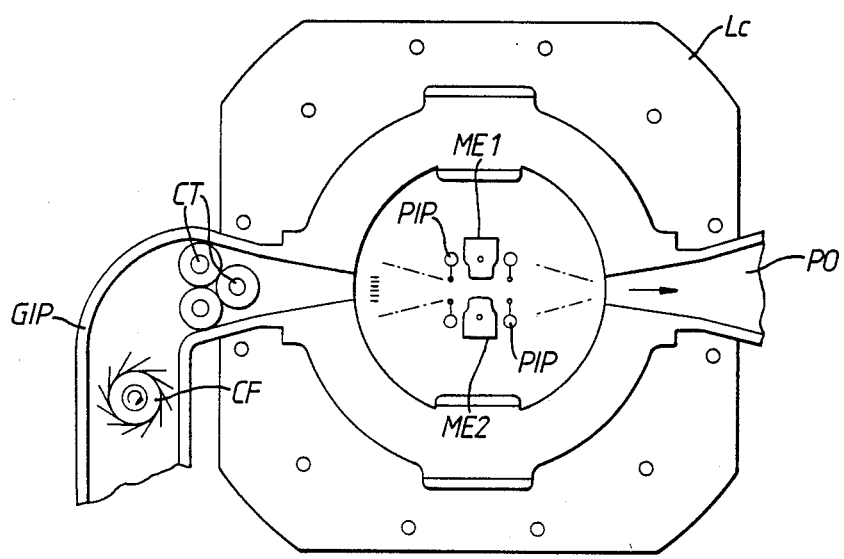
FIG. 2 is a schematic cross-section of the laser or discharge chamber showing a gas flow system for cooling the laser gas.

FIG. 2 is a schematic cross-section of the laser chamber showing a possible gas flow system, in which the gas input port GIP, comprising a cooling fan CF, ducts gas into the laser chamber LC over proprietary cooling tubes CT, the flow being laminar and not obstructed by P.I. pins PIP, to flow between the electrodes MEL 1 and 3 and then to exit via the outlet port PO from where it is recirculated back to the input port GIP. Additional or alternative cooling means may be provided by circulating coolant through ducts formed in the electrodes themselves.

The pressure vessel was first tested for pressure and vacuum requirements. Each particular slot section was adapted to cope with the individual requirements such as a high voltage feed-though (see FIG. 3), after which pressure and vacuum tests were repeated. In the light of the experience gained with this development device, a smaller laser could be constructed for push-button use on a mobile operational I.R. RADAR platform At the bottom of FIG. 3 the top of the support structure for the high pressure laser is also shown. This support structure allows a tubular rail (not shown) carrying optical elements to be decoupled mechanically and electrically from the main discharge section. Top and side dovetails (not shown) of the rail offer convenient mounting conditions for the optical components of the optical cavity. Characterization of the laser cavity is done by use of a CW - $CO_2$ discharge section. All optical components and computer cavity control systems used were tested before being implanted in the laser.

Figure 6:
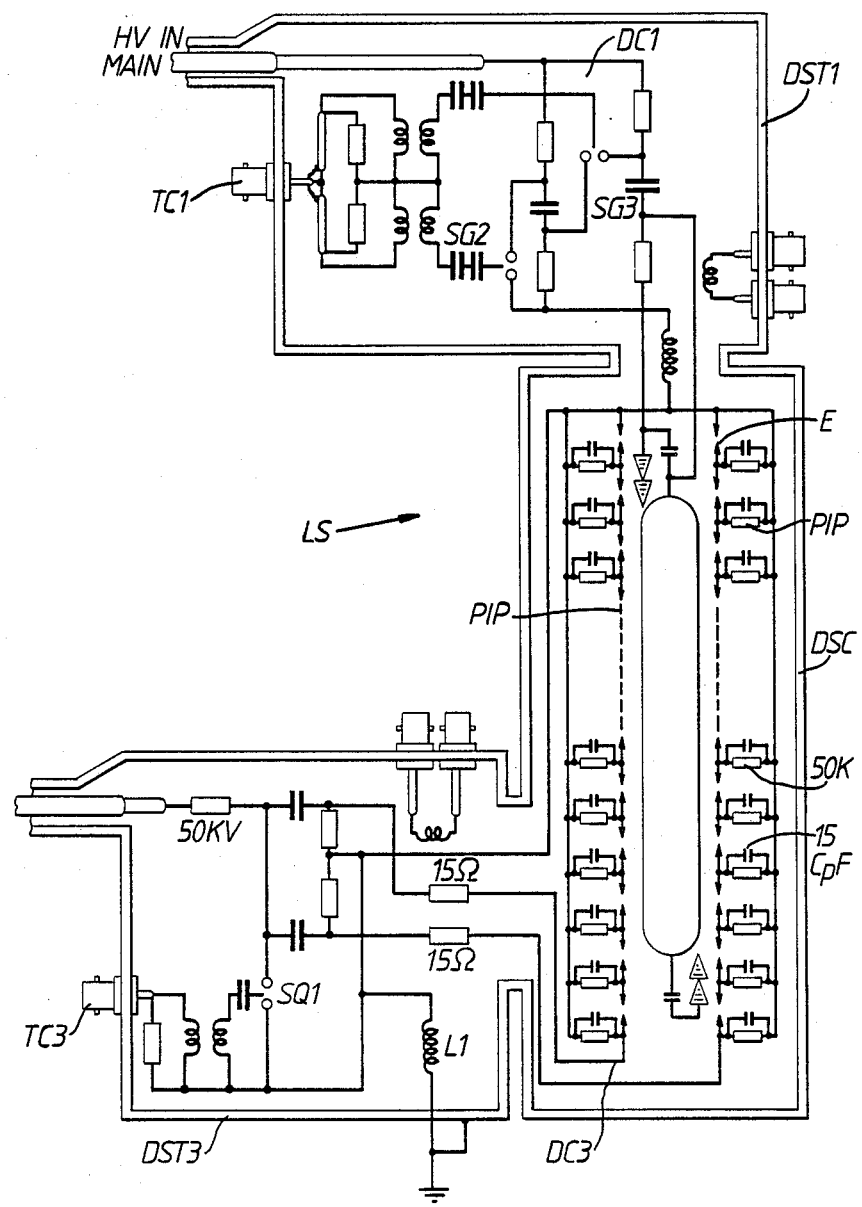
FIG. 6 is a diagrammatic representation of the main and pre-ionising discharge circuits and associated trigger circuits respectively and their housings.

The double screen constituted by the tubes 1, 3 is extended as indicated at DST1 & DST 3 respectively in FIG. 6 to house the main discharge circuit DC1 and its trigger TC1 and the pre-ionising discharge circuit DC3 and its trigger TC3 so that these circuits are housed within a double electromagnetic screen. The portions DST1 and DST3 may be separately formed and then made integral with the discharge chamber.

Figure 5:
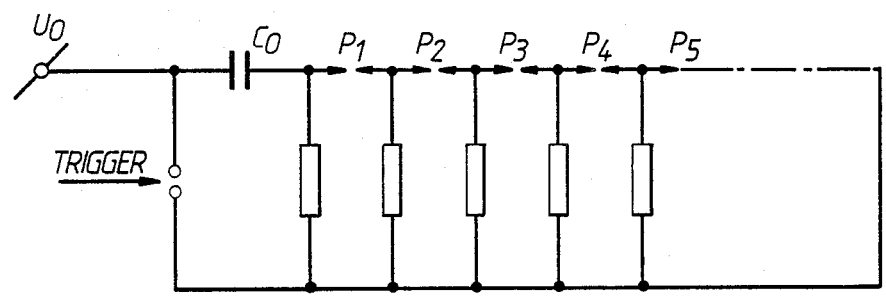
FIG. 5 is a diagram showing the essential circuit of the pre-ionising electrode unit.

FIG. 5 shows an array of pins PIP, the gap respectively between opposed pins being $\Omega$0.8 mm. Initially the storage capacitor Co is charged to a potential of 65 KV. After the spark-gap is triggered, the voltage rises on the first pin of gap P1. The second pin of gap P1 is at a low potential and the gap break down. All pins (see FIG. 5) are loaded with a resistor R in this instance of 50K $\Omega$ to form a high impedance for the incremental surge current. The potential across gap P2 rises until the second gap breaks down and this continues for the remaining gaps until all gas between the pins is ionised. After this sliding spark the discharge path avoids the 50K $\Omega$ resistors resulting in a low impedance and high current characteristic.

This simple configuration is an improvement over previously reported sliding spark TEA and MAL lasers. The main departure is use of four sliding spark arrays of pre-ionised pins PIP in a double sided geometry next to the top and bottom electrodes. The tungsten pins are symmetrically displaced with respect to the optical axis. Homogeneity of the ionization photons for the preconditioning of the main laping gap and the lack of obstruction to transverse gas flow are particular improvements in this set-up. The arc arrays on each side of the electrode are fed by different capacitors which makes it easier to match the circuit parameters, producing more uniform and critically damped breakdown which both boosts U.V. production and avoids erosion of the P.I. pins As indicated above the pre-ioniser is isolated from the main discharge so the delay between these two discharges can be tuned. Delay times are between 200 nsec to 1.5 $\mu$ sec to provide satisfactory plasma conditions.

The time interval between the surge currents at successive spark gap breakdowns is less than 1 nsec. For the 33 gaps this results in an overall delay of less than 33 nsec. It has been found that a delay of 75 nsec between the triggers of the P.I. and main bank is satisfactory. The optimal delay between P.I. and main discharge recommended is about 200 nsec. and is in close approximation to what was found.

After the initial runs with the laser the P.I. -unit was improved by introducing capacitors in parallel with the resistors (see FIG. 6) with a value of 180 pF each. Effectively the surge current is forced to charge and discharge these spark peaking capacitors, which extend the photon production.

Operation of the P.I. unit suggests the following:

(a) a double row of sparks with a 50% offset to one another gives improved uniformity compared with a single sided illumination.

(b) In order to achieve a reasonably homogeneous photon distribution to precondition the main electrode gap, a spark is required every 2 cm.

(c) To avoid tail off end-effects on the photonionization caused by the limited pre-ioniser length, the latter must exceed the electrode length; with the 250 mm long electrodes, a 300 mm P.I. is used.

(d) The most critical parameter is the distance of the spark array from the electrode centre-line and this should be minimized. The P.I. offset employed was between 2 and 5 cm.

Uniformity in pre-ionisation in the directions transverse to the main discharge current flow is more essential than uniformity in the parallel direction. Space charge effects distort the local electric field and the ionization rate, but smooth the plasma nonuniformities that develop during discharge initiation and create a uniform discharge.

The Marx bank (main discharge) and P.I. circuit has approximately a pulse power of $10^8$ W at a voltage of 50 KV and currents of 2 KA. This is in contrast with the low power networks of current electronic control and diagnostic equipment. Both must share the same wall plug facilities, which leads to earthing problems. Sensitive optical detectors with a $10^{-14}$ W diagnostic signal (1 $\mu$V into 100$\Omega$) make an isolation factor of $10^{22}$ necessary between power source and real optical diagnostics. It is also essential to be able to operate computers and real time diagnostics in a nearby vicinity and for the remote sensing equipment to be able to operate the computer controlled optical resonator for automated frequency selection and locking. The associated problems of electromagnetic interference in the communication field are similar, but in the present laser system they are distinguished as follows:

the circuitry uses a single pulse low repetition rate technology and no CW or quasi CW waveforms are used.

the pulse networks have higher peak currents.

Even if circuits are highly conducting, large e.m.f.'s will develop when surge currents with rise times of 50 nsec flow through them owing to the inductance of the current loop. This can be minimized by use of large flat conductor-geometry. The problem areas are multiple ground loops in the main discharge and pre-ioniser leads, trigger and diagnostics cables. Apart from the physical wiring there are the effects of stray capacity at high frequencies and the released electromagnetic radiation during the discharge, both of which add noise sources. The radiated energy will inductively couple with water and gas supplies or concrete reinforcement, which involve the surrounding building structure and influence the whole mains wiring. Total control of these circuit problems and interference factors is necessary to minimize pick-up. The approach adopted was to reduce these interference levels at the source rather than to rely on isolating everything else. That is, a complete double shielding enclosure was used to accommodate the high voltage and discharge circuitry which is effectively disconnected from other electronics during the discharge pulse.

Figure 7:
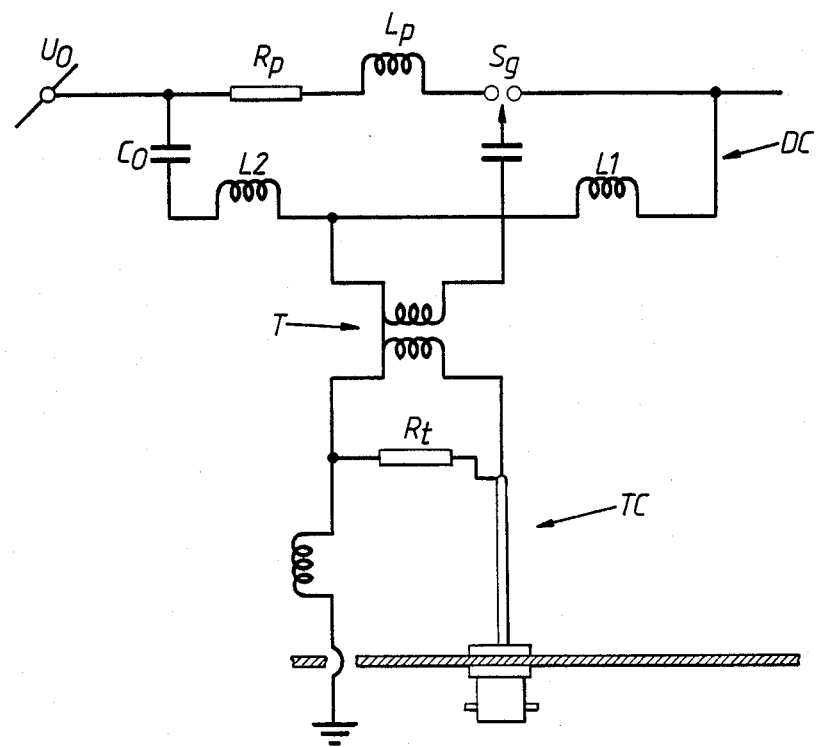
FIG. 7 is a circuit diagram of a discharge circuit in simplified form with an associated trigger circuit.

The main problem regarding external circuitry arises from the trigger units which have obviously to remain physically connected to the trigger unit to initiate the laser pulse. To indicate that effect, a simple representation is used of the Marx bank circuit with a condenser value $C_{01}$ of 5 nF and a charging voltage of 50 KV (see FIG. 7 which illustrates the simplified discharge network DC with trigger circuit TC). The trigger circuit comprises a transformer T through which a spark gap SG of the discharge circuit is activated by a pulse from the trigger circuit, the trigger circuit providing the earth return for the discharge circuit.

The plasma load is Lp and Rp representing the inductance and resistance respectively. The earth return side is divided in two parts with an inductance Lt1 and Lt2, with Lt2 assumed to be 1/10th of the total found previously to be about 0.4 $\mu$H.

Although the circuit inductance is very low, the generated e.m.f injects a voltage pulse on the earth lead which is unavoidable. Rt is a trimming resistor (see FIG. 7) which is initially assumed to be 0$\Omega$. In practise a 10 meter cable with an inductance of (10 $\mu$H) is used as a trigger cable. This inductance acts in parallel with the circuit inductance of 50 nH, so that a main current of 1.9 KA will induce currents in the order of 10 A in the braid of the coax cable. For the latter with a braid resistance of $10^{-2} \Omega$ m$^{-1}$ the imposed current transient will result in a voltage spike of 1.0 V on the general earth system. This voltage spike is minimized by maximizing the value of the trimming resistor Rt, the circuit is then virtually floating during the discharge with the current only affecting the appropriate conductors, completing a round trip between the capacitor places. In practise a value $R_t$ of 100$\Omega$ permitted reliable triggering with a jitter of 30 nsec., together with adequate isolation. For shielding purposes all leads were grouped onto small interconnection panels on the screening and the high voltage cable feedthroughs was accommodated within tubes, of length five times the diameter, to avoid E.M. radiation leaks. Likewise the braid of the coaxial cables were securely bound to the wall of the screening enclosure. The enclosure itself (see FIG. 6) was an extension of the high pressure vessel. All circuit and discharge devices were therefore within a continuous metal envelope, which should entail isolation over 60 dB better than obtained with a mesh enclosure. In the double wall screening used here, the outer screen was connected to ground and the inner was left floating.

This is shown in FIG. 6 which diagrammatically illustrates a Marx bank and P.I. discharge circuits with current diagnostic ports.

The single ground return lead for the entire circuitry is connected in series with a coil to avoid transient pulses on the earth lead from the P.I. and main discharge current.

The inner and outer vessels may be connected to earth via an impedance preferably frequency matched for noise related interference arising from the discharge.

The P.I. pins are grouped in two sections around the main electrode. Each P.I. section is separately connected with a 5 nF capacitor and fired with a common spark gap (SG1). The main electrode Marx bank has two spark gaps (SG2 and SG3) to switch the main discharge current. These are both triggered simultaneously. It was found that the simpler mechanism of triggering SG2 by over-volting caused to jitter.

I claim:

1. In a laser including a discharge chamber, the improvement wherein the discharge chamber comprises a plurality of vessels one located within another, wherein the innermost vessel is constructed to contain a lasing medium and discharge means operated by a high-voltage circuit for effecting lasing of the medium, said vessels collectively forming a multiple electromagnetic screen to contain electromagnetic radiation arising from the discharge means and the high-voltage circuit.

2. A laser according to claim 1, characterized in that the vessels are sealed together by annular seals disposed at axial ends of the vessels.

3. A laser according to claim 1, characterized in that the outermost vessel is electrically connected to ground.

4. A laser according to claim 1, characterized in that two vessels are employed.

5. A laser according to claim 1, wherein said high-voltage circuit includes a discharge circuit and a trigger circuit for triggering the discharge circuit to initiate a discharge between discharge electrodes of the laser on operation of the discharge circuit by the trigger circuit, and wherein said circuits are housed within said innermost vessel.

6. A laser according to claim 1, wherein said high-voltage circuit includes a pre-ionizing electrode array, a discharge circuit, and a trigger circuit for initiating a discharge of the pre-ionizing circuit, and wherein the pre-ionizing electrode array and the discharge and trigger circuits are housed within said innermost vessel.

7. A laser according to claim 1, wherein said high-voltage circuit comprises a discharge circuit which operates by release of stored electrical energy on closure of a circuit make/break device, and a trigger circuit inductively coupled to the discharge circuit to effect closure of a circuit make/break device, and wherein the trigger circuit provides a ground return for the discharge circuit and the trigger circuit includes a current-limiting resistor or a switch to isolate the trigger circuit from a supply on pulsing of the laser, in order to prevent the imposition of a voltage pulse on the ground return of the trigger circuit upon operation of the discharge circuit.

* * * * *